United States Patent
Fujimoto et al.

(10) Patent No.: US 6,289,739 B1
(45) Date of Patent: Sep. 18, 2001

(54) SACRIFICIAL SPECIMEN FOR USE IN MONITORING LONG-TERM STRESS INTENSITY OF STRUCTURE AND METHOD OF USING THE SAME

(75) Inventors: Yukio Fujimoto; Eiji Shintaku; Kunihiro Hamada, all of Higashihiroshima (JP)

(73) Assignee: Hiroshima University, Higashihiroshima (JP)

( * ) Notice: Subject to any disclaimer, the term of this patent is extended or adjusted under 35 U.S.C. 154(b) by 0 days.

(21) Appl. No.: 09/459,893

(22) Filed: Dec. 14, 1999

(30) Foreign Application Priority Data

Dec. 17, 1998 (JP) .................................. 10-358725

(51) Int. Cl.$^7$ .................................. G01N 19/08
(52) U.S. Cl. .................................. 73/799
(58) Field of Search ............... 73/762, 786, 799, 73/808

(56) References Cited

U.S. PATENT DOCUMENTS

| | | | |
|---|---|---|---|
| 4,409,841 | * 10/1983 | Archer | 73/762 |
| 4,580,520 | * 4/1986 | Archer | 73/762 |
| 5,493,511 | * 2/1996 | Wincheski et al. | 73/799 |
| 5,789,680 | 8/1998 | Fujimoto | 73/719 |

* cited by examiner

*Primary Examiner*—Max Noori
(74) *Attorney, Agent, or Firm*—Oliff & Berridge, PLC (57) ABSTRACT

A sacrificial specimen for use in monitoring a long-term stress intensity of a structure including a main body made of a metal and having an artificial crack formed at a central region thereof, and a pair of metal or synthetic resin thin plates each having a slit formed at a central region, said pair of thin plates being cemented together with interposing the main body therebetween such that said artificial crack is exposed outside through the slits. The sacrificial specimen is cemented onto a structure whose long-term stress intensity has to be monitored such that a central portion corresponding to the central regions of the main body and thin plates is not secured to the structure surface. When the sacrificial specimen is subjected to stress, the slits formed in the thin plates are deformed largely and a fatigue crack is produced in the main body such that the fatigue crack extends from the artificial crack. Stress applied to the sacrificial specimen is amplified and fatigue due to the amplified stress is accumulated in the sacrificial specimen, the long-term stress intensity of the structure can be monitored accurately.

19 Claims, 8 Drawing Sheets

SACRIFICIAL SPECIMEN FOR USE IN MONITORING LONG-TERM STRESS INTENSITY OF STRUCTURE AND METHOD OF USING THE SAME

BACKGROUND OF THE INVENTION

1. Field of the Invention

The present invention relates to a sacrificial specimen for use in monitoring long-term stress intensity of various structures to predict stress conditions of the structures such as ships, bridges, marine structures and towers which are subjected to natural environments such as winds and waves, railway bridges and loads which are subjected to traffic stress, and cranes used in bays and factories. By means of the sacrificial specimen, a load process of varying stress to structures can be stored in the sacrificial specimen as fatigue damage, and therefore by monitoring the fatigue damage of the sacrificial specimen, it is possible to predict the long-term stress intensity of structures. The present invention also relates to a method of using such a sacrificial specimen for monitoring long-term stress intensity of structures.

2. Related Art Statement

Structures are subjected to various kinds of stresses which vary slowly for a long time. Stresses caused by natural environments such as winds, waves and earthquakes are very complicated. Furthermore, since a large scale structure has a particularly complicated construction, it is sometimes very difficult to grasp stresses on various structural members. Therefore, in order to keep safety of structures as well as to realize a safety designing, it is very important to predict stress conditions of structures by monitoring.

There have been proposed several methods of monitoring stress condition of a structure under use. A stress monitoring method using strain gauges has been widely utilized. In this method, strain gauges have to be secured to portions at which the stress condition should be monitored. Moreover, this method requires an electric power source, switch boxes and strain detecting circuits for strain gauges, and furthermore a recorder is required for recording a history of strain over a rather long time period. Although these components have become rather small, monitoring cost is increased particularly in a large size structure in which a larger number of strain gauges have to be arranged. It should be further noted that wiring operation for connecting various equipments via electrical conductors becomes cumbersome and expensive.

In another stress monitoring method, there are provided precise displacement measuring devices instead of the strain gauges. However, this method still requires an electric power source, a recorder and wiring system.

One of the inventors of the present application has proposed, in U.S. Pat. No. 5,789,680, a sacrificial specimen for use in the fatigue damage monitoring system for predicting a timing at which fatigue damage will actually appear in a structure on the basis of information obtained by monitoring a fatigue damage condition of the sacrificial specimen fixed to the structure. In this known sacrificial specimen, a process of changing stress is not directly monitored, but an accumulation of stress is stored in the sacrificial specimen. This kind of sacrificial specimen is generally provided at a portion of a structure at which stresses are concentrated and a serious fatigue damage might be produced. Therefore, the known sacrificial specimen is constructed to generate a fatigue damage when the sacrificial specimen is subjected to such a large stress by a number of times. It is apparent that such a sacrificial specimen could not be utilized to monitoring a long-term stress intensity of a structure, because the sacrificial specimen is not subjected to a stress having a magnitude which is sufficient for producing a fatigue damage in the sacrificial specimen.

SUMMARY OF THE INVENTION

The present invention has for its object to provide a novel and useful sacrificial specimen which can monitor a stress condition of a structure to predict a long-term stress intensity of the structure.

It is another object of the invention to provide a sacrificial specimen, in which a stress applied to a structure can be amplified.

According to the invention, a sacrificial specimen for use in monitoring a long-term stress intensity of a structure comprises:

a main body in a form of a thin metal plate and having an artificial crack formed at a central region viewed in a longitudinal direction of the main body; and a pair of thin plates each having a slit which is formed at a central region viewed in a longitudinal direction and extends in a lateral direction perpendicular to the longitudinal direction, said pair of thin plates being cemented to opposite surfaces of said main body such that said artificial crack formed in the main body is exposed outside through said slits formed in the thin plates.

In a preferable embodiment of the sacrificial specimen according to the invention, said main body is formed by a copper plate having a thickness of about 0.1 mm, and said thin plates are formed by an epoxy resin plate reinforced with glass fibers and having a thickness of about 0.3 mm. The artificial crack is formed to have a width of about 0.1 mm and a length of about 5 mm, and the slit has a width of about 2 mm and a length of about 30 mm.

The present invention also relates to a method of using the above mentioned sacrificial specimen, in which a rear surface of the sacrificial specimen is cemented onto a surface of a structure whose long-term stress intensity is to be monitored such that the sacrificial specimen is secured to the structure at an area except for a central portion at which the artificial crack and slits are formed. In this case, a synthetic resin film may be interposed between the central portion of the sacrificial specimen and the structure surface.

DESCRIPTION OF THE PREFERRED EMBODIMENT

Figure 1A:
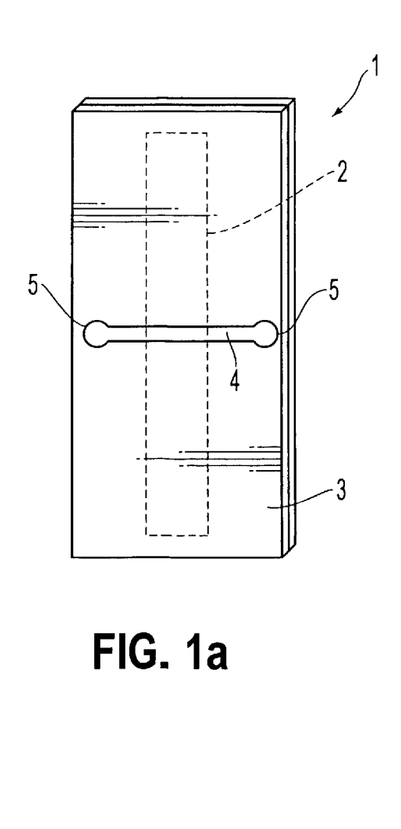
FIGS. 1a–1d are perspective and cross sectional views showing an embodiment of the sacrificial specimen according to the invention.

FIGS. 1a–1d show an embodiment of the sacrificial specimen according to the invention. The sacrificial specimen 1 comprises a main body 2 formed by a thin metal plate and a pair of thin plates 3 made of metal or resin. The thin main body 1 is sandwiched between the thin plates 3. The thin plates 3 have slit-like through holes 4 formed at central regions viewed in a longitudinal direction of the plates. As best shown in FIG. 1a, both end portions 5 of the slits 4 are formed to be round so that undesired crack is hardly produced in the thin plates 3.

Figure 1B:
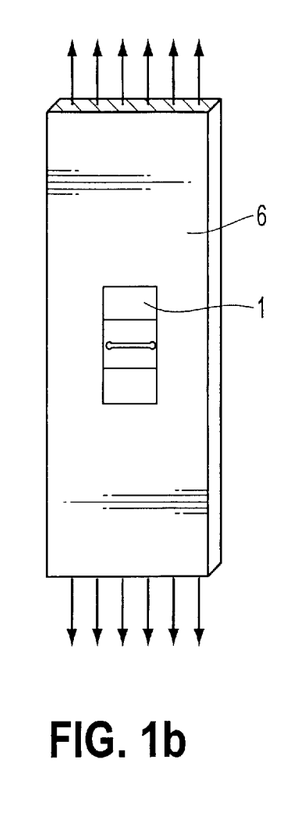
Figure 1C:
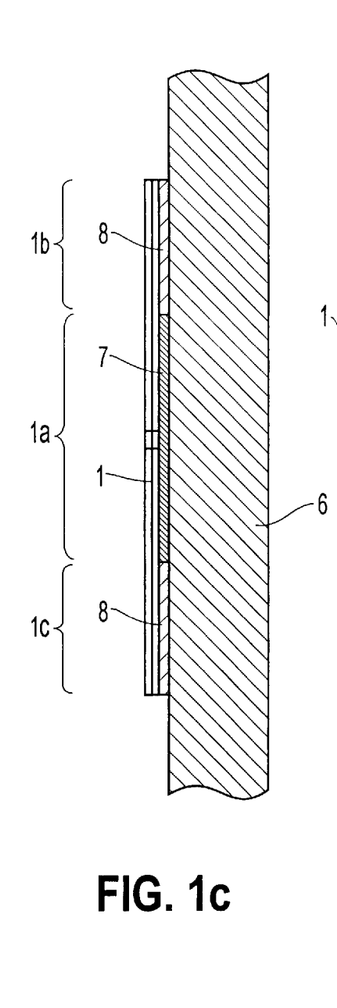

As shown in FIG. 1b, the sacrificial specimen 1 is secured or cemented to a structural member 6 whose long-term stress intensity is to be monitored. Upon cementing the sacrificial specimen 1 to the structural member 6, a film 7 made of fluoro resin is inserted between a central portion 1a of the specimen 1 and the structural member 6, and adhesive 8 is applied to rear surfaces of end portions 1b and 1c of the sacrificial specimen 1 existing on both sides of the central portion 1a viewed in the longitudinal direction.

Figure 1D:
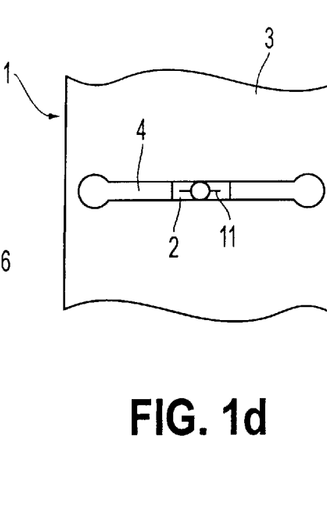

As best shown in FIG. 1d, the main body 2 has an artificial crack 11 formed at a central region such that the artificial crack is exposed outside through the slits 4. It should be noted that the artificial crack 11 extends in parallel with the slits 4.

In the sacrificial specimen 1 according to the invention, stress applied to the structural member 6 can be physically amplified, and thus even very small stress can be accumulated as fatigue damage in the sacrificial specimen. Therefore, it is possible to monitor the long-term stress intensity of the structural member 6. This stress amplifying mechanism will be explained hereinbelow.

Figure 2A:
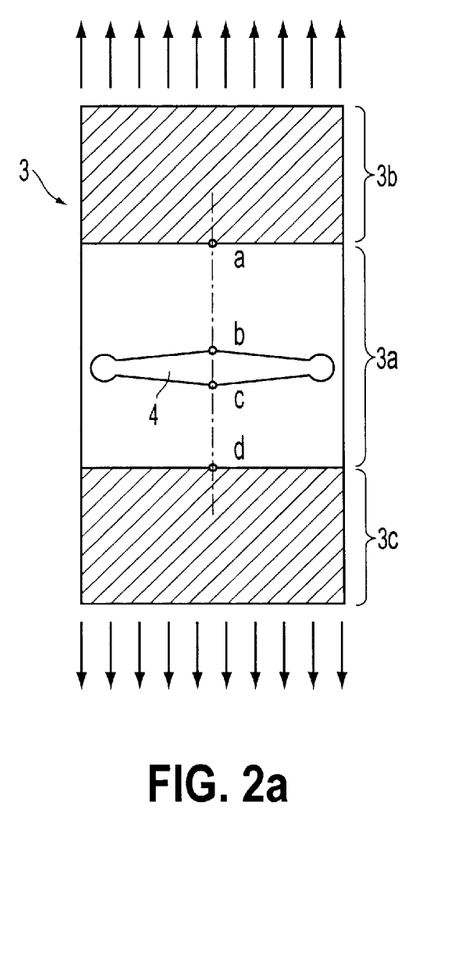
FIGS. 2a and 2b are schematic plan views explaining a mechanism for physically amplifying a stress in the sacrificial specimen according to the invention.
Figure 2B:
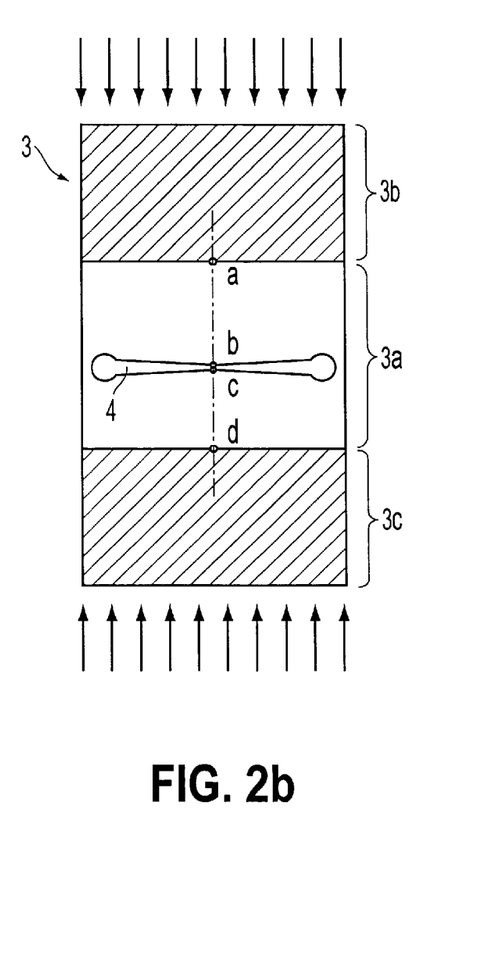

FIGS. 2a and 2b are plan views showing the deformation of a thin plate 3 having a slit 4 formed at a central region to extend in a lateral direction. As explained above, the sacrificial specimen 1 is secured to the structural member 6 only at its end portions and the central portion is not secured to the structural member. In FIG. 2a, end portions 3b and 3c (shown by hatching) of the thin plate 3 are secured to the structural member, and therefore when a tensile or expansion force is applied to the thin plate 3 in its longitudinal direction as illustrated in FIG. 2a, the central portion 3a including the slit 4 is deformed or expanded. In this case, since the slit 4 could not resist the stress, both end portions of the slit 4 are hardly deformed and the deformation is concentrated at a center of the slit 4. Therefore, the slit 4 is deformed into a convex shape. That is to say, a distance between points b and c is increased largely, while a distance between points a and b as well as a distance between points c and d are not substantially changed.

When a compressive force is applied to the thin plate 3 as depicted in FIG. 2b, the central portion 3a of the thin plate 3 is deformed such that the slit 4 is deformed into a concave shape. In other words, the distance between points b and c is decreased, but the distances between points a and b as well as between points c and d are not substantially decreased.

In this manner, when the thin plate 3 is secured to the structural member 6 at its both end portions 3b and 3c such that the central portion 3a of the thin plate 3 can be freely deformed, the distance between the points b and c at the center of the slit 4 is changed largely when the tensile or compressive force is applied to the thin plate 3 in its longitudinal direction which is perpendicular to the extending direction of the slit 4.

Figure 3:
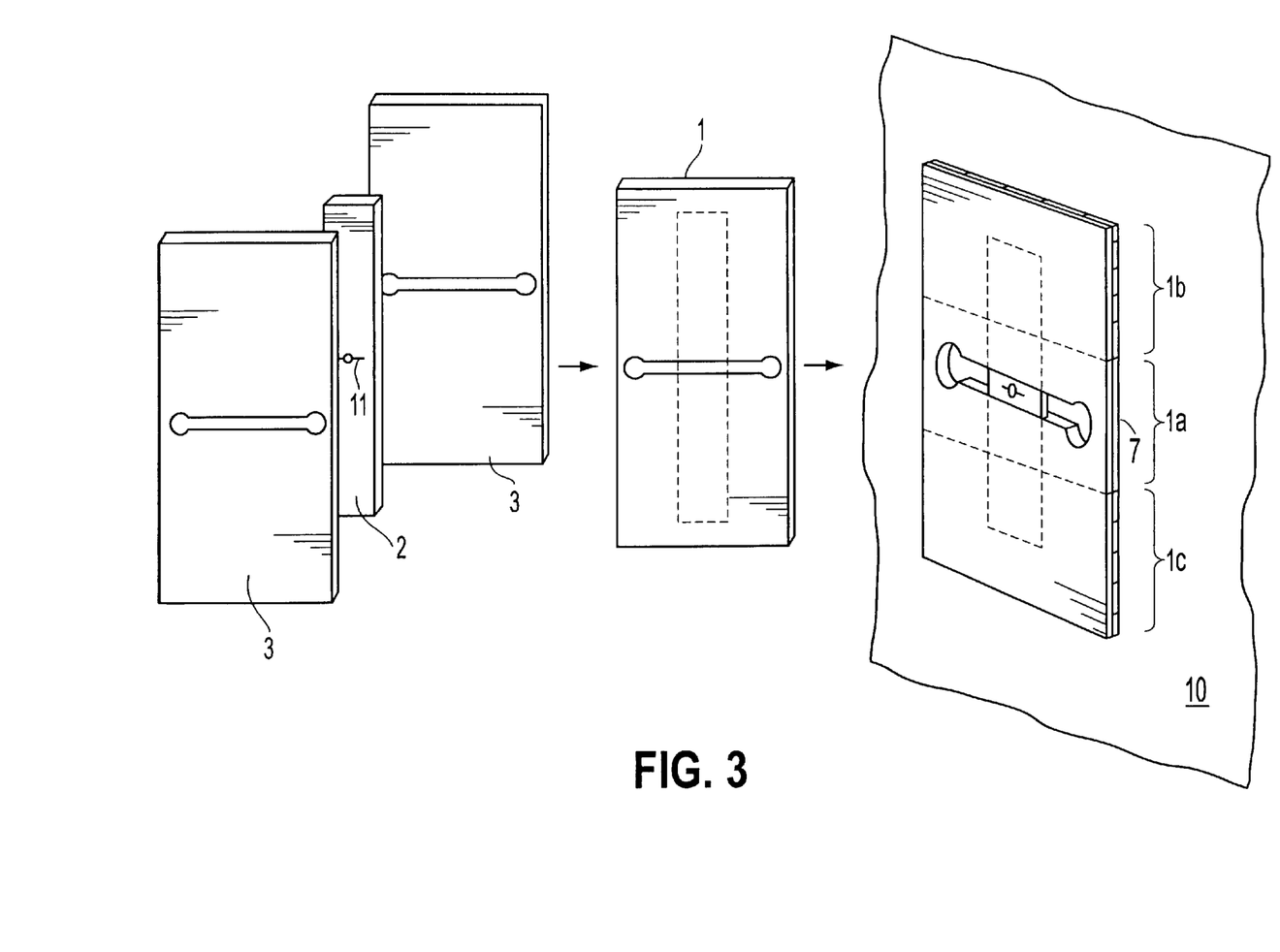
FIG. 3 is a schematic perspective view depicting a manner of securing the sacrificial specimen onto a structure.

In the sacrificial specimen 1 according to the invention, as illustrated in FIG. 3, the main body 2 having the artificial crack 11 formed in the central region is sandwiched between the thin plates 3 such that the artificial crack is exposed outside through the slits 4 formed in the thin plates 3. It should be noted that the artificial crack 11 formed in the main body 2 extends in parallel with the slits 4 formed in the thin plates 3 and has a length substantially shorter than a length of the slits 4. The main body 2 and thin plates 3 are cemented together with a suitable adhesive agent, and therefore when the central portions 3a of the thin plates 3 are deformed, the central region of the main body 2 is subjected to large stress and the artificial crack 11 can easily extend or grow.

In case of securing the sacrificial specimen 1 onto a structure 10, the film 7 made of fluoro resin is first cemented on the rear surface of the sacrificial specimen 1 at its central portion 1a, and then the sacrificial specimen 1 is cemented to a surface of the structure 10 by means of a suitable adhesive at both end portions 1b and 1c such that the central portion 1a of the sacrificial specimen 1 is not secured to the structure 10.

Figure 4:
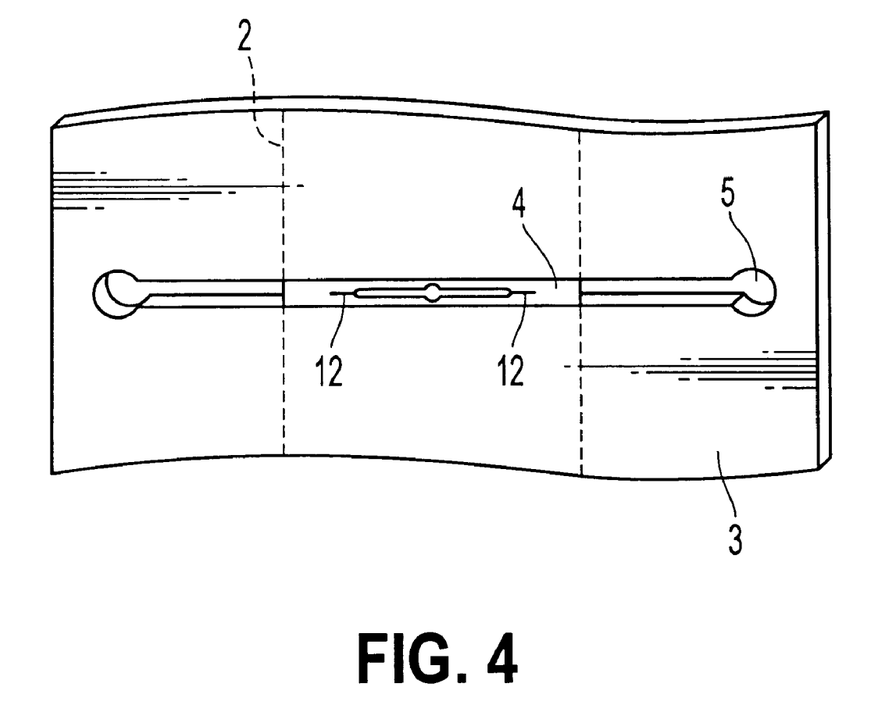
FIG. 4 is a perspective view showing a slit portion of the sacrificial specimen according to the invention on an enlarged scale.

FIG. 4 is a perspective view showing a part of the central portion 1a of the sacrificial specimen 1 secured to the structure. When the structure is subjected to the repeated stress by the tensile and compressive forces, the slits 4 formed in the thin plates 3 are largely deformed as depicted in FIGS. 2a and 2b, and therefore the main body 2 is also deformed to produce a fatigue crack 12 as shown in FIG. 4. This fatigue crack 12 is growing larger in accordance with an increase in an accumulated stress. Therefore, by monitoring the fatigue crack 12 formed in the main body 2, it is possible to predict the long-term stress intensity of the structure.

Now the construction of the sacrificial specimen 1 of the present embodiment will be explained in detail. The main body 2 is formed by a pure copper plate having a thickness of 0.1 mm, a length of 90 mm and a width of 5 mm. In the central region of the main body 2, the artificial crack 11 is formed by a wire cutting to have a width of 0.1 mm and a length of 5 mm. End portions of the sacrificial crack 11 are finished to have a round configuration.

Each of the thin plates 3 is formed by a glass fiber containing epoxy resin thin plate having a thickness of 0.3 mm, a length of 100 mm and a width of 36 mm. The slit 4 has a width of 2 mm and a length of 30 mm. The round end portions 5 of the slit 4 have a diameter of 4 mm. The thin plate 3 has a modulus of direct elasticity of about 21.6 GPa.

The main body 1 and thin plates 3 are cemented together by the adhesive agent made of epoxy resin. The fluoro resin film 7 is cemented to the rear surface of the sacrificial specimen 1 over a length of 40 mm, and then the end portions 1b and 1c of the sacrificial specimen 1 are cemented onto the structure by means of the epoxy resin adhesive agent.

It should be noted that stress amplifying factor of the sacrificial specimen 1 may be changed or adjusted by changing various parameters of the main body 2 and thin plates 3 such as material, thickness, width, length, as well as parameters of the slit 4 and artificially formed crack 11 such as width, length and shape. By suitably setting these parameters, it is possible to realize a sacrificial specimen having desired characteristics.

In order to investigate fatigue characteristics of the sacrificial specimen 1 according to the invention, the sacrificial specimen is cemented onto a surface of a flat mild steel, and then the flat mild steel is secured to a fatigue testing machine with oil pressure servo-control. Under completely reversed tension and compression axial force, the sacrificial specimen is subjected to the stress in a periodical manner. During the test, the fatigue condition of the main body 2 is monitored with the aid of a microscope having a magnification of 50. The fatigue crack 12 grows from both ends of the artificial crack 11 substantially uniformly. During the test, the cemented portions are not pealed off and the main body 2 is not buckled.

Figure 5:
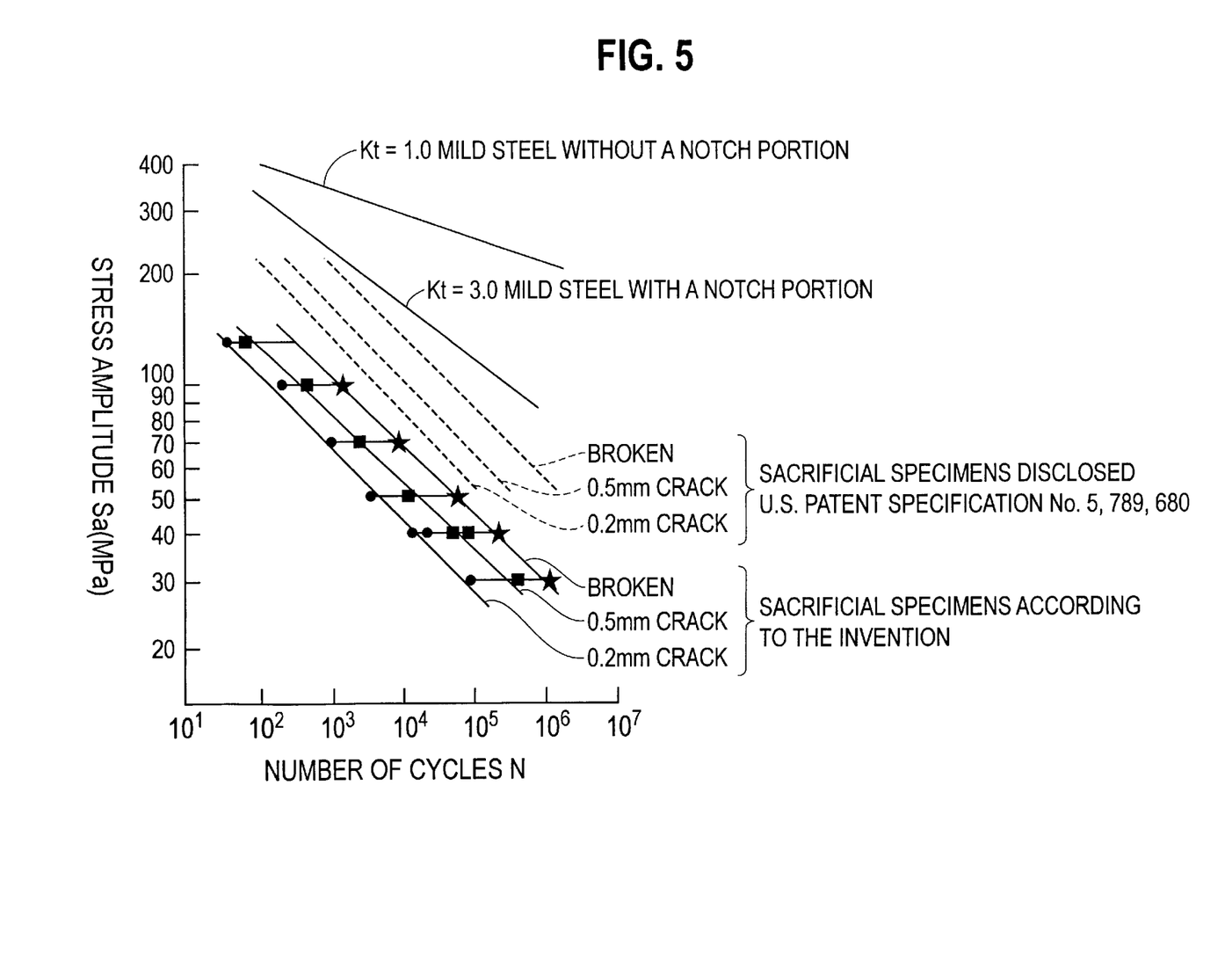
FIG. 5 is a graph representing a relationship between a stress magnitude (Sa) applied to the sacrificial specimen and the number of respective stress (N)

FIG. 5 is a graph showing an Sa-N curve (Stress amplitude-Number of cycles), in which a vertical axis denotes a stress amplitude applied to the flat steel Sa and a horizontal axis represents the number of cycles N. Black dots show a life time when the fatigue crack 12 extends from the tips of the artificial crack 12 over 0.2 mm, black squares a life time when the fatigue crack 12 grows over 0.5 mm, and black stars denote a life time when the main body 2 is cut completely by the fatigue crack 12. In FIG. 5, solid curves denote Sa-N diagrams of flat mild steel made of SS400 without and with a notch portion having a stress concentration factor of 3.0. These curves are formed by gathering data from publications. Furthermore, in FIG. 5, three dotted curves represent Sa-N diagrams of the known sacrificial specimens developed by one of the inventors and disclosed in the above mentioned U.S. Pat. No. 5,789,680.

As can be seen from FIG. 5, the known sacrificial specimen developed by one of the inventors has a stress concentration factor of 6.0 for the fatigue crack having a length of 0.2 mm. Contrary to this, the sacrificial specimen according to the present invention produces a fatigue crack at a substantially lower stress and its life time is shortened. This is due to the fact that in the sacrificial specimen according to the invention, the stress is amplified and the thus amplified stress is applied to the main body. Such a feature is specific to the sacrificial specimen according to the invention and could not be easily deduced from the known sacrificial specimen.

Figure 6:
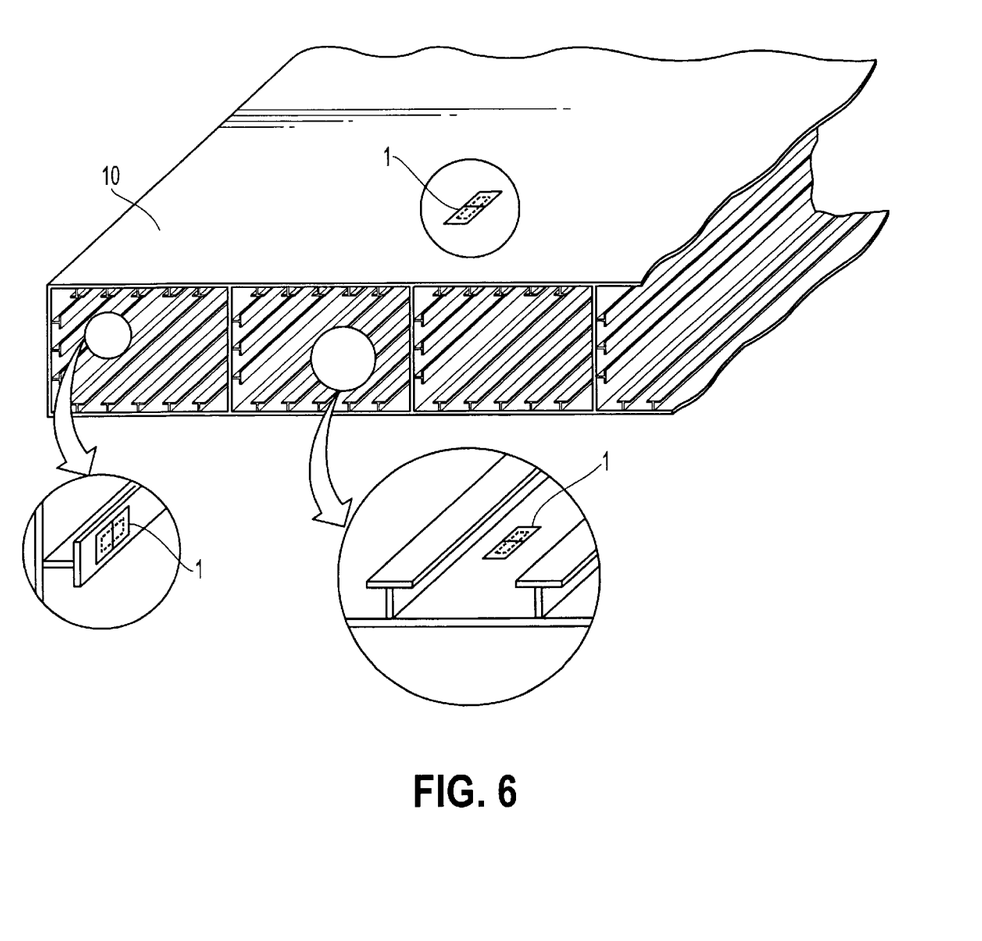
FIG. 6 is a perspective view showing a condition of the sacrificial specimen secured onto a structure.

The sacrificial specimen 1 according to the invention is secured to the structure 10 as illustrated in FIG. 6. In this case, it is no more necessary to provide equipments such as electric power source, detecting circuit and wiring. In this manner, the sacrificial specimen according to the invention can be provided in a very simple manner.

Figure 7:
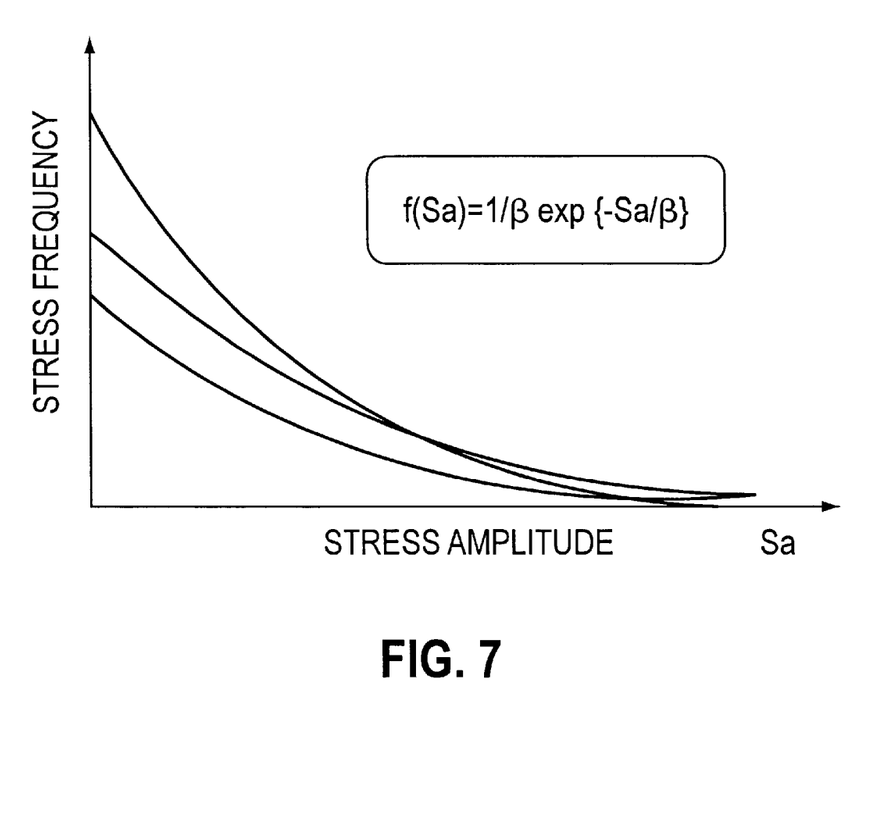
FIG. 7 is a graph denoting a relationship between the stress frequency and the stress magnitude (Sa)

The long-term stress intensity of the structure can be predicted in the following manner. A frequency distribution of stress applied to the structure by the natural environments such as wind and wave has been known to follow an exponential distribution or weibull distribution. A frequency distribution of traffic stress to which bridges are subjected has been known to some extent. However, parameters for defining a long-term stress intensity are unknown in many cases. p It is now assumed that the stress frequency distribution is represented by exponential distributions as shown in FIG. 7. In this case, the stress frequency distribution will be determined when a parameter $\beta$ is known. A number of stress frequency distributions are prepared for exponential distributions having different $\beta$, and life times of the sacrificial specimen for these stress frequency distributions are predicted by means of the linear cumulative fatigue damage rule. There is an error between a life time predicted by the linear cumulative fatigue damage rule and an actual life time, and this error has to be considered in accordance with a critical fatigue damage value. This critical fatigue damage value may be derived by conducting the fatigue test for the sacrificial specimen under the exponential stress. From the above, it is possible to determine a relationship between the parameter $\beta$ and the life time N of the sacrificial specimen as shown in FIG. 8.

Figure 8:
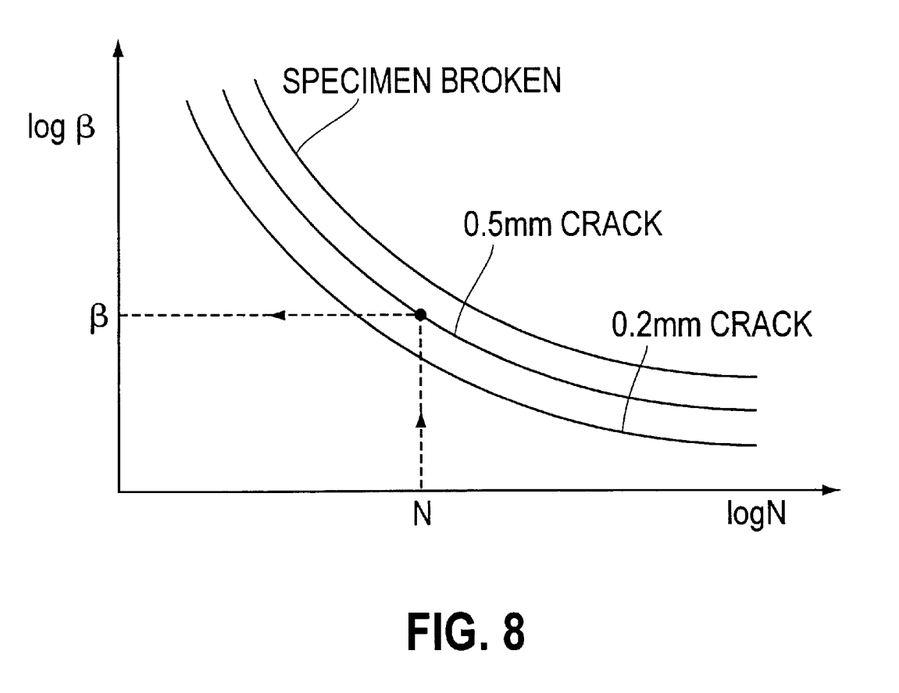
FIG. 8 is a graph explaining a manner of predicting the long-term stress intensity of a structure.

For instance, when a fatigue crack having a length of 0.5 mm is detected at the number of repetitive stress N, $\beta$ may be estimated as shown by arrows in FIG. 8. In this manner, the long-term stress distribution may be determined. Also in the weibull distribution in which the stress frequency distribution is determined by both shape parameter and scale parameter, the scale parameter may be determined in a similar manner by fixing the shape parameter to a suitable value.

As can be seen from FIG. 5, the sacrificial specimen according to the invention has a very long life time from a time at which a fatigue crack is generated to a time at which the main body of the sacrificial specimen is broken or cut into two portions. When a fatigue crack is monitored during this long life time, the long-term stress intensity of the structure can be predicted.

As explained above in detail, in the sacrificial specimen according to the invention, a stress is amplified by the thin plates having the slits and the thus amplified stress is applied to the main body having the artificially formed crack. Therefore, a fatigue crack can be easily produced in the main body even with s small stress. In this manner, the long-term stress intensity of a structure can be monitored accurately. A number of points of the structure can be monitored for a long time in an easy and precise manner without requiring various equipments such as electric power source, detecting circuits and wiriness, and a safety of the structure can be guaranteed and the design of the structure can be improved. It should be noted that no electric power is required, it is no more necessary to provide a protection against explosion.

The present invention is not limited only to the embodiment explained above, but many alternations and modifications can be conceived by those skilled in the art within the scope of the invention.

What is claimed is:

1. A sacrificial specimen for use in monitoring a long-term stress intensity of a structure comprising:

a main body in a form of a thin metal plate and having an artificial crack formed at a central region viewed in a longitudinal direction of the main body; and a pair of thin plates each having a slit which is formed at a central region viewed in a longitudinal direction and extends in a lateral direction perpendicular to the longitudinal direction, said pair of thin plates being cemented to opposite surfaces of said main body such that said artificial crack formed in the main body is exposed outside through said slits formed in the thin plates.

2. A sacrificial specimen as claimed in claim 1, wherein said main body is formed by a copper plate having a thickness of about 0.1 mm.

3. A sacrificial specimen as claimed in claim 2, wherein said main body has a length of about 90 mm and a width of about 10 mm, and said artificial crack has a width of about 0.1 mm and a length of about 5 mm.

4. A sacrificial specimen as claimed in claim 3, wherein said artificial crack extends in opposite directions from a circular hole formed in the main body at its center.

5. A sacrificial specimen as claimed in claim 3, wherein said pair of thin plates are made of a synthetic resin or a metal.

6. A sacrificial specimen as claimed in claim 5, wherein each of said pair of thin plates is formed by an epoxy resin thin plate having a thickness of about 0.3 mm, a width of about 36 mm and a length of about 100 mm.

7. A sacrificial specimen as claimed in claim 6, wherein said slit formed in each of said thin plates has a width of about 2 mm and a length of about 30 mm.

8. A sacrificial specimen as claimed in claim 5, wherein said main body and thin plates are cemented together with an epoxy resin adhesive agent.

9. A sacrificial specimen as claimed in claim 1, wherein said sacrificial specimen further comprises a synthetic resin film secured to a rear surface at a central portion of the sacrificial specimen.

10. A method of using a sacrificial specimen as claimed in claim 1, wherein a rear surface of the sacrificial specimen is cemented onto a surface of a structure whose long-term stress intensity is to be monitored such that the sacrificial specimen is secured to the structure at an area except for a central portion at which the artificial crack and slits are formed.

11. A method as claimed in claim 10, wherein a synthetic resin film is interposed between the central portion of the sacrificial specimen and the structure surface.

12. A method of using a sacrificial specimen as claimed in claim 2, wherein a rear surface of the sacrificial specimen is cemented onto a surface of a structure whose long-term stress intensity is to be monitored such that the sacrificial specimen is secured to the structure at an area except for a central portion at which the artificial crack and slits are formed.

13. A method of using a sacrificial specimen as claimed in claim 3, wherein a rear surface of the sacrificial specimen is cemented onto a surface of a structure whose long-term stress intensity is to be monitored such that the sacrificial specimen is secured to the structure at an area except for a central portion at which the artificial crack and slits are formed.

14. A method of using a sacrificial specimen as claimed in claim 4, wherein a rear surface of the sacrificial specimen is cemented onto a surface of a structure whose long-term stress intensity is to be monitored such that the sacrificial specimen is secured to the structure at an area except for a central portion at which the artificial crack and slits are formed.

15. A method of using a sacrificial specimen as claimed in claim 5, wherein a rear surface of the sacrificial specimen is cemented onto a surface of a structure whose long-term stress intensity is to be monitored such that the sacrificial specimen is secured to the structure at an area except for a central portion at which the artificial crack and slits are formed.

16. A method of using a sacrificial specimen as claimed in claim 6, wherein a rear surface of the sacrificial specimen is cemented onto a surface of a structure whose long-term stress intensity is to be monitored such that the sacrificial specimen is secured to the structure at an area except for a central portion at which the artificial crack and slits are formed.

17. A method of using a sacrificial specimen as claimed in claim 7, wherein a rear surface of the sacrificial specimen is cemented onto a surface of a structure whose long-term stress intensity is to be monitored such that the sacrificial specimen is secured to the structure at an area except for a central portion at which the artificial crack and slits are formed.

18. A method of using a sacrificial specimen as claimed in claim 8, wherein a rear surface of the sacrificial specimen is cemented onto a surface of a structure whose long-term stress intensity is to be monitored such that the sacrificial specimen is secured to the structure at an area except for a central portion at which the artificial crack and slits are formed.

19. A method of using a sacrificial specimen as claimed in claim 9, wherein a rear surface of the sacrificial specimen is cemented onto a surface of a structure whose long-term stress intensity is to be monitored such that the sacrificial specimen is secured to the structure at an area except for a central portion at which the artificial crack and slits are formed.

* * * * *